(12) United States Patent
Martins

(10) Patent No.: US 10,779,800 B2
(45) Date of Patent: Sep. 22, 2020

(54) ULTRASOUND IMAGING TRANSDUCER ELECTRICAL NOISE COMPENSATION

(71) Applicant: B-K MEDICAL APS, Herlev (DK)

(72) Inventor: Bo Martins, Rodovre (DK)

(73) Assignee: B-K Medical ApS, Herlev (DK)

( * ) Notice: Subject to any disclaimer, the term of this patent is extended or adjusted under 35 U.S.C. 154(b) by 965 days.

(21) Appl. No.: 15/366,487

(22) Filed: Dec. 1, 2016

(65) Prior Publication Data
US 2018/0153521 A1 Jun. 7, 2018

(51) Int. Cl.
*A61B 8/00* (2006.01)
*A61B 8/08* (2006.01)
*G01S 7/52* (2006.01)
*G01S 15/89* (2006.01)

(52) U.S. Cl.
CPC .......... *A61B 8/5269* (2013.01); *A61B 8/5207* (2013.01); *A61B 8/54* (2013.01); *G01S 7/52077* (2013.01); *G01S 7/52085* (2013.01); *A61B 8/4483* (2013.01); *A61B 8/461* (2013.01); *G01S 15/8995* (2013.01)

(58) Field of Classification Search
None
See application file for complete search history.

(56) References Cited

U.S. PATENT DOCUMENTS 6,293,912 B1 *  9/2001  Sørensen ............ G01S 7/52026
                                                    600/437
2006/0293596 A1 * 12/2006 Jago ..................... G01S 7/52046
                                                    600/437

* cited by examiner

*Primary Examiner* — Joel F Brutus
(74) *Attorney, Agent, or Firm* — Anthony M. Del Zoppo, III; Daugherty & Del Zoppo Co., LPA

(57) ABSTRACT

An ultrasound imaging system (300) includes one or more transducing elements (304). The ultrasound imaging system further includes a system controller (330) configured to control the one or more transducing elements to receive for a predetermined time duration without first transmitting and produce a noise only signal. The system controller is further configured to control the one or more transducing elements to transmit a set of pulses which causes the one or more transducing elements to transmit a pressures wave and receive echo waves generated in response to the transmitted pressures wave and produce an echo plus noise signal indicative thereof. The ultrasound imaging system further includes a noise processor (320) that compensates the echo plus noise signal with the noise only signal, creating a denoised signal, which is displayed.

20 Claims, 3 Drawing Sheets

ULTRASOUND IMAGING TRANSDUCER ELECTRICAL NOISE COMPENSATION

TECHNICAL FIELD

The following generally relates to ultrasound imaging and more particularly to compensating an ultrasound image for electrical noise of the ultrasound imaging transducer receiving the echo signal used to generate the ultrasound image.

BACKGROUND

An ultrasound imaging system includes at least a transducer array with one or more transducing elements. For scanning a patient, the transducer array is positioned against the subject, and one or more of the transducing elements are excited to transmit a pressure wave which traverses the subject. An echo wave is produced in response to the pressure wave interacting with matter such as tissue, blood, etc. in the subject. The one or more transducing elements receive the echo wave and produce an electrical signal. The electrical signal is indicative of both the received echo wave and electrical noise of the transducer array.

The transmitted and echo waves are attenuated as they traverse the subject. As such, prior to processing the electrical signal, time gain compensation (TGC) is applied to amplify it so that a signal for deeper tissue has approximately a same amplitude as a signal for more superficial tissue. The amplified signal includes an amplified echo signal and an amplified electrical noise signal, which increases with depth. Depending on the depth, the echo wave may be attenuated such that its amplitude is on an order of the noise, and the amplified noise will appear as a greyish background onto which the amplified ultrasound image appears.

As the greyish background image impacts contrast, a user may prefer to see the ultrasound image without the noise. To achieve this, the user manipulates the TGC curve based on depth so that the background noise is less visible at the cost of lowering echo signal brightness. FIG. 1 shows an example image in which the front-end gain of the system amplifies the echo signal and the noise at larger depths to a degree that the noise manifests in a greyish background 102. FIG. 2 shows the image after the noise is reduced through the TGC curve to remove much of the greyish background 102.

Unfortunately, the above approach to reducing visible noise requires the system provide at least a sufficient analog gain for difficult cases and/or the user manually adjust the TGC whenever the echo strength, the electrical noise strength and/or the processing gain changes. Such situations where this occurs include, e.g. a depth change, a beamforming change, a change in compound parameters, harmonics on/off, pulsed wave Doppler being enabled, a change to a mode that needs lower transmit voltage in order not to exceed predetermined (e.g., FDA) limits or burst contrast bubbles.

In order for the user to avoid adjusting the TGC curve, a maximum gain is pre-specified for the clinical preset. Unfortunately, a maximum gain defines a hard limitation in penetration and creates an unnatural boundary in the displayed ultrasound image. Furthermore, it is time-consuming trying to define a correct maximum value and it depends on a sensitivity of the particular transducer used to create the preset. As such, there is an unresolved need for another approach to process such data.

SUMMARY

Aspects of the application address the above matters, and others.

In one aspect, an ultrasound imaging system includes one or more transducing elements. The ultrasound imaging system further includes a system controller configured to control the one or more transducing elements to receive for a predetermined time duration without first transmitting and produce a noise only signal. The system controller is further configured to control the one or more transducing elements to transmit a set of pulses which causes the one or more transducing elements to transmit a pressures wave and receive echo waves generated in response to the transmitted pressures wave and produce an echo plus noise signal indicative thereof. The ultrasound imaging system further includes a noise processor that compensates the echo plus noise signal with the noise only signal, creating a denoised signal, which is displayed.

In another aspect, a method includes receiving, with one or more transducing elements and for a predetermined time duration without first transmitting, and producing, by the one or more transducing elements, a noise only signal for the predetermined time duration, which is indicative of an electrical noise of the one or more transducing elements. The method further includes transmitting, with the one or more transducing elements, a pressure wave, receiving, with the one or more transducing elements, echo waves created in response to the pressure wave interacting with matter, and generating an echo plus electrical noise signal from the received echo waves. The method further includes correcting the echo plus electrical noise signal with the noise only signal, creating a corrected echo signal. The method further includes displaying the corrected echo signal.

In another aspect, a computer readable medium is encoded with non-transitory computer executable instructions which when executed by a processor causes the processor to: control one or more transducing elements to receive, for a predetermined time duration without first transmitting, wherein the one or more transducing elements produce a noise only signal for the predetermined time duration, excite the one or more transducing elements to transmit a pressure wave, control the one or more transducing elements to receive echo waves created in response to the pressure wave interacting with matter, generate an echo plus noise signal with the received echo waves, correct echo plus noise signal with the noise only signal, creating a corrected echo signal, and display the corrected echo signal.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
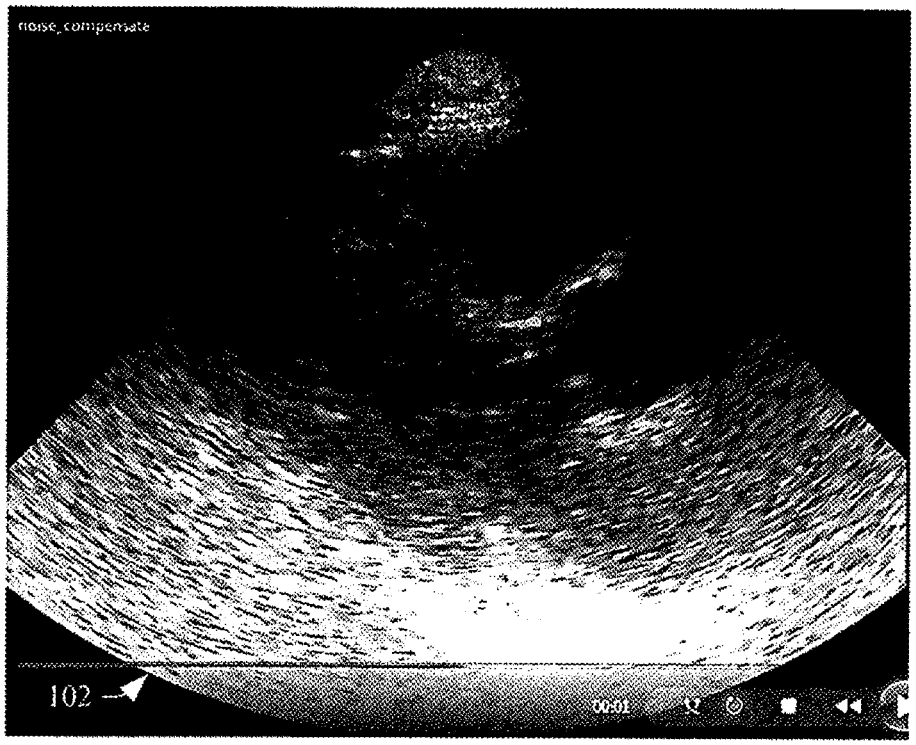
FIG. 1 shows an example ultrasound image in which the front-end gain of the system amplifies the signal and the noise at larger depths to a degree that the noise manifests in a greyish background.
Figure 2:
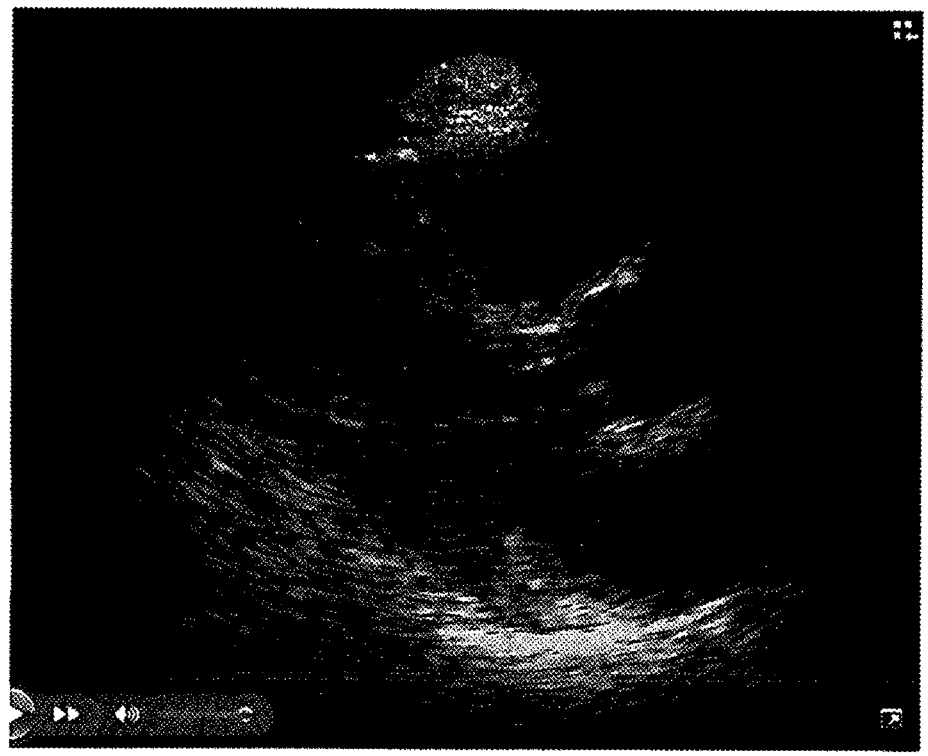
FIG. 2 shows the example ultrasound image of FIG. 1 after the noise is reduced through the TGC curve, which reduces the greyish background.
Figure 3:
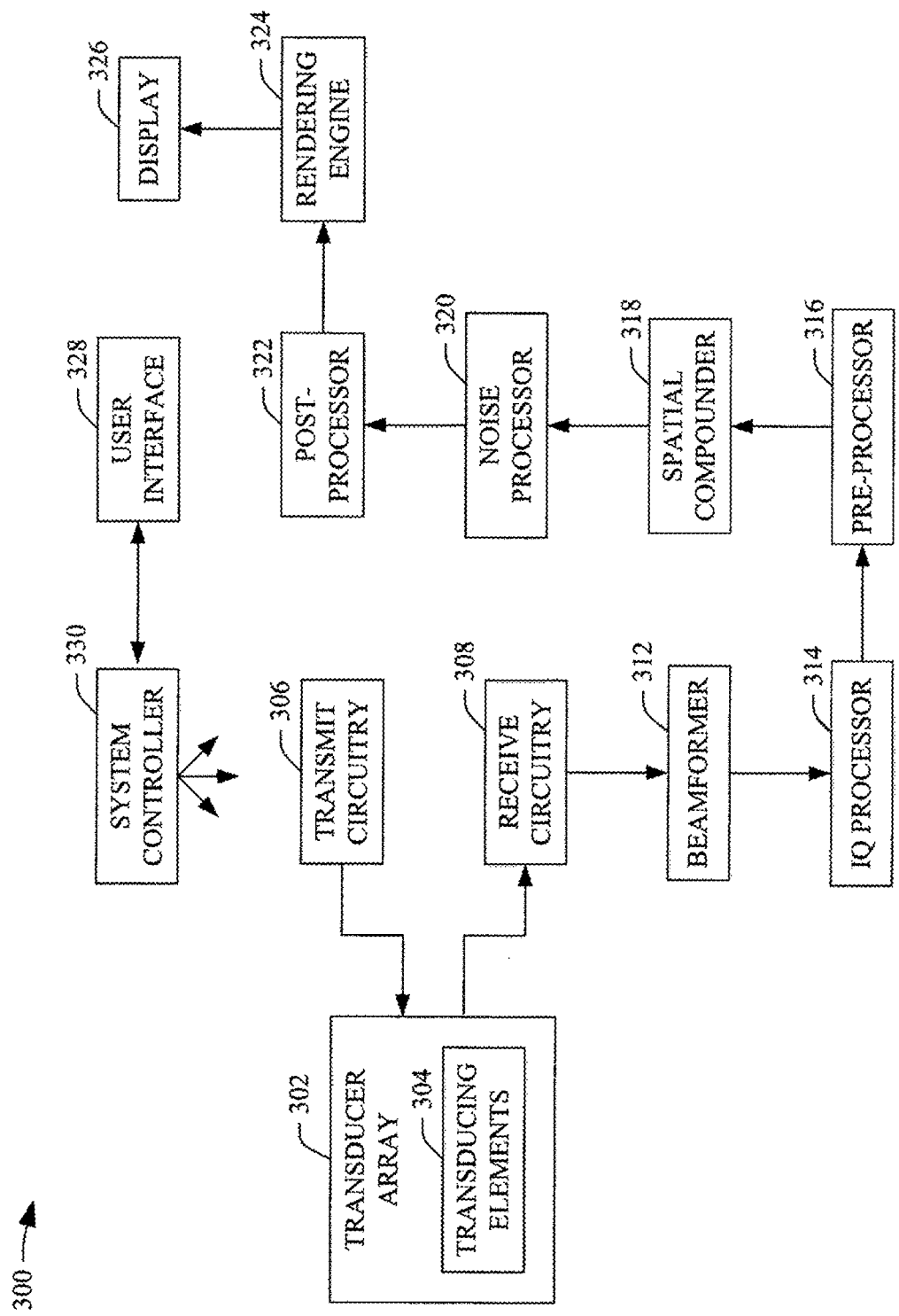
FIG. 3 schematically illustrates an example imaging system with a noise processor.

FIG. 3 schematically illustrates an example ultrasound imaging system 300. The ultrasound imaging system 300 includes a one- or two-dimensional transducer array 302 with one or more transducing elements 304. The transducing elements 304 are configured to emit a pressure wave in response to begin excited by an electrical signal or pulse. The transducing elements 304 are further configured to receive an echo pressure wave, which is generated in response to the emitted pressure wave interacting with structure (e.g., tissue, blood, etc.), and produce an electrical or echo signal indicative of the echo pressure wave.

Transmit circuitry 306 generates pulses that excite a set of the transducing elements 304 to transmit a pressure wave. Receive circuitry 308 receives the electrical signal. In one instance, for a particular depth, the transducing elements 304 are controlled to receive without first transmitting, and acquire a partial set of lines or partial image, followed by transmitting and receiving to acquire a full set of lines for an image. If another depth is desired, this same process of a fast or quick acquisition to capture a few lines before any transmission followed by transmission and reception to acquire more lines is repeated for the other depth(s).

By way of non-limiting example, the transducing elements 304 can receive and acquire five (5) to fifteen (15) lines, e.g., over 2.5 to 30 milliseconds (ms), and then transmit and receive and acquire fifty (50) to five hundred (500) lines. The first acquisition captures only electrical noise of the transducer array 302, and the subsequent acquisition captures echo signal plus the electrical noise. For spatial compounding, the above is performed at each of a set of different angles at a same position by maintaining the position of the transducer array 302 at a fixed position and transmitting the beam at different angles via electronic beam steering and/or electronically or manual controlled mechanical steering of the array.

A beamformer 312 is configured to beamform the electrical noise only signal and the echo plus electrical noise signal. For B-mode imaging, the beamforming may include delaying the signals from each of the elements 304 and summing the delayed signals, producing radiofrequency (RF) data. An in-phase quadrature (IQ) processor 314 is configured to at least convert the RF-data to the complex-value IQ domain, producing IQ data. This can be achieved by multiplying the RF-signal by a complex sinusoid signal, e.g., I=RF×cos(wt), and Q=RF×−sin(wt).

A pre-processor 316 is configured to process the IQ data and generate envelope data by computing an amplitude of the complex IQ signal for every sample in every scan line. The pre-processor 316 also resamples the envelope data and compresses a dynamic range of resampled envelope data to the display resolution (e.g., from 16 bit to 8 bit). A spatial compounder 318 is configured to spatially compound (i.e., aligns and combines frames that are acquired at different times and at different angles of insonation) the frames to form a single compounded frame for the electrical noise signal and the echo plus noise signal.

A noise processor 320 is configured to process the compounded frames and compensate the echo plus noise signal for the measured electrical noise. In one instance, this includes using the electrical noise only image, which is indicative of noise as a function of depth, to remove or reduce the electrical noise in an echo plus electrical noise image. As described in greater detail below, this can be achieved with or without auto gain, and/or with user TGC and user overall gain. In one instance, this approach does not limit a maximum amount of gain in penetration at least because the noise, in the end, can be removed from the displayed image.

A post-processor 322 is configured to process the electrical noise compensated signal. In one instance, this includes converting the data back to its original format. A rendering engine 322 visually presents the noise reduced image via a display monitor 324. A user interface 328 includes one or more input devices (e.g., a button, a knob, a slider, a touch pad, etc.) and/or one or more output devices (e.g., a display screen, lights, a speaker, etc.). The user interface 328 can be used to select an imaging mode such as imaging with noise compensation with or without autogain as described herein, control acquisition, etc.

A system controller 330 is configured to control one or more of the components of the system 300. For example, in one instance the system controller 324 controls the transmit and receive circuitries 306 and 308 to sequentially acquire noise only data at a depth of interest and then echo signal data at the depth of interest, for one or more depths of interest. For this, the system controller 324 controls the transmit circuitry 306 to control the transducing elements 304 to receive without first transmitting, followed by a transmit and receive operation.

In one instance, the transducer array 302 is part of a probe and the transmit circuitry 306, the receive circuitry 308, the beamformer 312, the IQ processor 314, the pre-processor 316, the spatial compounder 318, the noise processor 320, the post-processor 322, the rendering engine 324, the display 326, the user interface 328, and the controller 330 are part of a separate console such as a computing system. Communication there between can be through a wired (e.g., a cable and electro-mechanical interfaces) and/or wireless communication channel. In this instance, the console can be similar to a portable computer such as a laptop, a notebook, etc., with additional hardware and/or software for ultrasound imaging. The console can be docked to a docketing station and used.

Alternatively, the console can be part (fixed or removable) of a mobile or portable cart system with wheels, casters, rollers, or the like, which can be moved around. In this instance, the display 326 may be separate from the console and connected thereto through a wired and/or wireless communication channel. Where the cart includes a docking interface, the laptop or notebook computer type console can be interfaced with the cart and used. An example of a cart system where the console can be selectively installed and removed is described in US publication 2011/0118562 A1, entitled "Portable ultrasound scanner," and filed on Nov. 37, 2009, which is incorporated herein in its entirety by reference.

Alternatively, the transducer array 302 is part of a probe and the transmit circuitry 306, the receive circuitry 308, the beamformer 312, the IQ processor 314, the pre-processor 316, the spatial compounder 318, the noise processor 320, the post-processor 322, the rendering engine 324, the display 326, the user interface 328, and the controller 330 are housed within a hand-held ultrasound apparatus where the housing mechanically supports and/or encloses the components therein. The transducer array 302 and/or the display 326 can be part of the housing, being structurally integrated or part of a surface or end of the hand-held ultrasound apparatus. An example of a hand-held device is in U.S. Pat. No. 7,699,776, entitled "Intuitive Ultrasonic Imaging System and Related Method Thereof," and filed on Mar. 6, 2003, which is incorporated herein in its entirety by reference.

Figure 4:
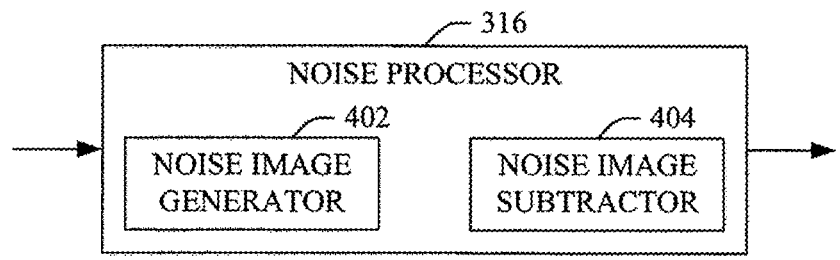
FIG. 4 schematically illustrates an example of the noise processor.
Figure 5:
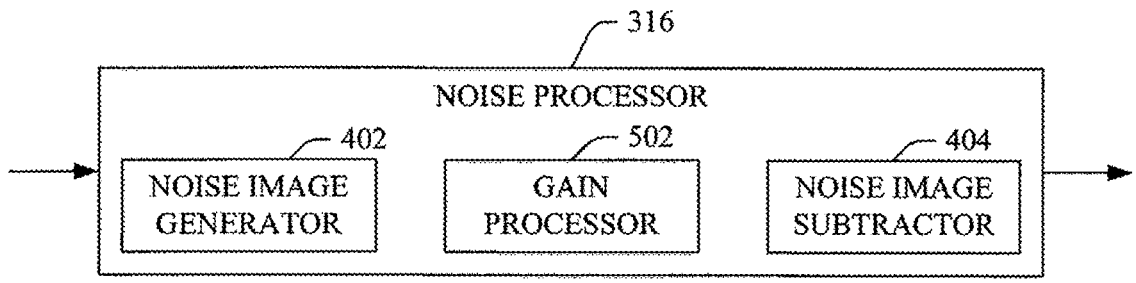
FIG. 5 schematically illustrates another example of the noise processor.

FIGS. 4 and 5 schematically illustrates examples of the noise processor 316. In FIG. 4, the noise processor 316 removes electrical noise with no autogain. In FIG. 5, the noise processor 316 removes electrical noise and applies autogain.

In FIG. 4, the noise processor 316 includes a noise image generator 402. The noise image generator 402 takes the partial set of lines corresponding to electrical noise only and creates a noise image by expanding the partial set of lines to the number of lines acquired for the echo plus electrical noise signal (the full number of lines). This can be achieved by computing an average of the partial set of lines to form a typical line and copying the typical line for every one of the full number of lines. In another aspect, the typical line may also be smoothed by a one-dimensional FIR or IIR filter prior to copying it. The noise image provides a measurement (and not an estimate) of an amplitude of the noise as a function of depth.

In FIG. 4, the noise processor 316 further includes a noise image subtractor 404. The noise image subtractor 404 subtracts, sample by sample, the electrical noise image from the echo signal plus electrical noise image. The output of the noise processor 316 is a de-noised image, or an image compensated with a measurement of the electrical noise. Since the electrical noise is depth dependent, the brightness in the de-noised image in the axial direction (top to bottom), relative to the echo signal plus electrical noise image, will decrease in brightness as a function of depth.

The noise processor 316 of FIG. 5 is substantially the same as the noise processor 316 of FIG. 4 except the noise processor 316 of FIG. 5 further includes a gain processor 502. The gain processor 502 applies a depth dependent gain and a lateral or line dependent gain to both the electrical noise image and the echo plus electrical noise image. As a result, the brightness of the de-noise image will vary in depth and laterally (left to right) along each line.

In a variation, the pre-processor 316 does not does process the IQ data or perform envelope detection or resampling, but instead compresses the RF data with user TGC and user overall gain. Similar to FIG. 4, the compounded frames are processed by the noise processor 316, with the output being processed by the post-processor 322, as described herein.

Figure 6:
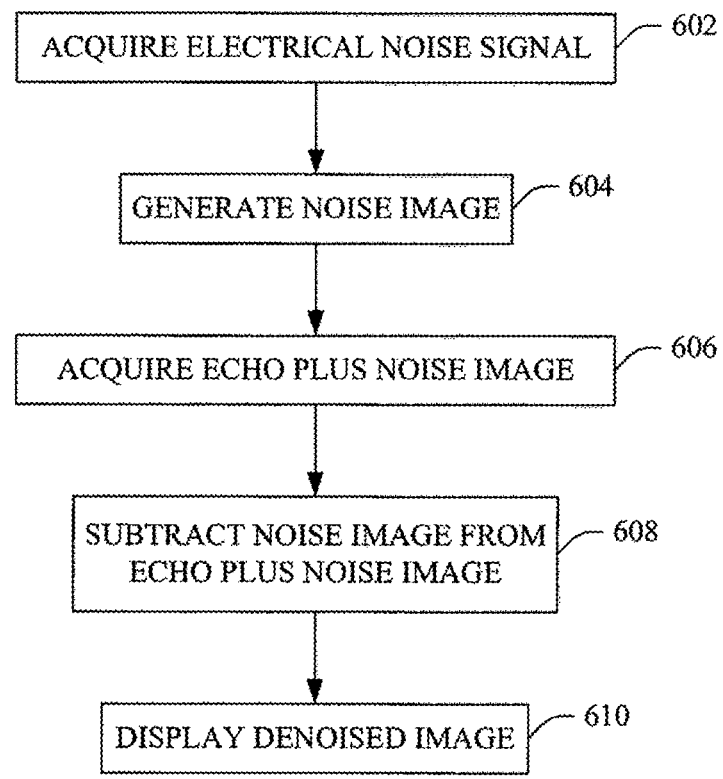
FIG. 6 illustrates an example method in accordance with an embodiment herein.

FIG. 6 illustrates an example method. It is to be appreciated that the following order and/or steps is not limiting. For example, step 604 could occur concurrently with step 604 or after step 604. Furthermore, another embodiment may have more, less and/or a different step.

At 602, the transducer 302 array is controlled to receive over a predetermined time duration without first transmitting an ultrasound signal and produce a partial set of lines indicative of only electrical noise of the transducer and a dependency of the electrical noise on depth, as described herein and/or otherwise.

At 604, the partial set of lines is expanded to form a noise only image with a, amplitude of the noise a function of depth, as described herein and/or otherwise.

At 606, the transducer array is controlled to transmit and receive and produce a full set of lines indicative of an amplitude of the echo plus electrical noise signal and the dependency of the electrical noise on depth, thereby providing an echo plus electrical noise image, as described herein and/or otherwise.

At 608, the noise only image is subtracted from the echo plus electrical noise image, which compensates for the depth dependent electrical noise as a function of depth, and produces a denoised image, as described herein and/or otherwise.

At 610, the denoise image is displayed. As discussed herein, the denoised image is displayed without visible noise but with full visibility of a desired signal that exceeds the noise, e.g., by just a small amount.

The approach described herein enables autogain that is independent of framerate. The measurement is independent of framerate unlike methods that are based on cross-correlation between different image frames. This approach, at least, is robust in that no image analysis is involved in determining the noise level, incorporates the current fidelity of a transducer (which is not constant over time), and/or is adaptive to user interaction. This includes changing between fundamental mode and harmonics, activating pulsed-wave Doppler which may reduce the transmit voltage in order not to heat the transducer beyond predetermined limits (e.g., FDA limits), changing the number of compound angles which affects the signal to noise ratio, changing the number of received beams which affects the signal to noise ratio, changing the front-end gain and/or other interaction.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
one or more transducing elements;
a system controller configured to control the one or more transducing elements to receive for a predetermined time duration without first transmitting and produce a noise only signal and then control the one or more transducing elements to transmit a set of pulses which causes the one or more transducing elements to transmit a pressures wave and receive echo waves generated in response to the pressures wave transmitted by the one or more transducing elements and produce an echo plus noise signal indicative thereof, wherein the system controller is configured to control the one or more transducing elements to acquire a first number of lines for the predetermined time duration and a second number of lines when receiving the echo waves, wherein the second number of lines is greater than the first number of lines; and
a noise processor configured to expand the first number of lines to a same number of lines as the second number of lines which creates an electrical noise only image that is indicative of the electrical noise as a function of depth and compensate the echo plus noise signal with the created electrical noise only signal, which creates a denoised signal, which is displayed.

2. The ultrasound imaging system of claim 1, wherein the first number of lines includes five to fifteen lines.

3. The ultrasound imaging system of claim 2, wherein the second number of lines includes fifty to five hundred lines.

4. The ultrasound imaging system of claim 3, further comprising: a beamformer, an IQ processor, and a pre-preprocessor configured to process the five to fifteen lines and the fifty to five hundred lines.

5. The ultrasound imaging system of claim 4, wherein the noise processor includes a noise image generator configured to expand the processed five to fifteen lines to create a set of fifty to five hundred lines, which create the electrical noise only image that is indicative of the electrical noise as the function of depth.

6. The ultrasound imaging system of claim 5, wherein the processed fifty to five hundred lines provides an echo plus electrical noise image, and wherein the noise processor further comprises: a noise image subtractor configured to subtract the noise only image from the echo plus electrical noise image to create a denoised image.

7. The ultrasound imaging system of claim 6, wherein the noise image subtractor subtracts the noise only image on a sample by sample basis.

8. The ultrasound imaging system of claim 7, wherein the noise processor is configured to amplify both the echo plus electrical noise image and the noise only image prior to the subtraction.

9. The ultrasound imaging system of claim 1, where the predetermined time duration is on an order of 2.5 to 30 milliseconds.

10. The ultrasound imaging system of claim 1, further comprising:
a post-processor configured to process an output of the noise processor; and
a rendering engine configured to process the out of the post-processor and display the denoised image on a display.

11. A method, comprising:
receiving, with one or more transducing elements and for a predetermined time duration without first transmitting;
producing, by the one or more transducing elements, a noise only signal for the predetermined time duration, which is indicative of an electrical noise of the one or more transducing elements, wherein the noise only signal includes a first number of lines;
transmitting, with the one or more transducing elements, a pressure wave;
receiving, with the one or more transducing elements, echo waves created in response to the pressure wave interacting with matter;
generating an echo plus electrical noise signal from the received echo waves;
expanding the first number of lines of the noise only signal to a second number of lines, wherein the second number of lines is greater than the first number of lines;
correcting the echo plus electrical noise signal with the noise only signal with the second number of lines, creating a corrected echo signal; and
displaying the corrected echo signal.

12. The method of claim 11, wherein the first number of lines includes five to fifteen lines.

13. The method of claim 12, wherein the second number of lines includes fifty to five hundred lines.

14. The method of claim 13, further comprising:
amplifying the echo plus electrical noise signal and the noise only signal; and
subtracting the amplified noise only signal from the amplified echo plus electrical noise signal.

15. The method of claim 14, where amplifying the echo plus electrical noise signal and the noise only signal comprises applying a depth dependent gain.

16. The method of claim 15, where amplifying the echo plus electrical noise signal and the noise only signal comprises applying a lateral dependent gain.

17. The method of claim 12, where the predetermined time duration is on an order of 2.5 to 30 milliseconds.

18. The method of claim 12, wherein the echo plus electrical noise signal includes fifty to five hundred lines.

19. The method of claim 18, wherein correcting echo plus electrical noise signal comprises: subtracting the noise only signal from the echo plus electrical noise signal.

20. A computer readable medium encoded with non-transitory computer executable instructions which when executed by a processor causes the processor to:
control one or more transducing elements to receive, for a predetermined time duration without first transmitting, wherein the one or more transducing elements produce a noise only signal with five to fifteen lines for the predetermined time duration;
excite the one or more transducing elements to transmit a pressure wave;
control the one or more transducing elements to receive echo waves created in response to the pressure wave interacting with matter;
generate an echo plus noise signal with the received echo waves;
expand the five to fifteen lines to fifty to five hundred lines;
correct the echo plus noise signal with the noise only signal with the fifty to five hundred lines; and
display the corrected echo plus noise signal.

* * * * *